United States Patent [19]
Aviram et al.

[11] Patent Number: 5,644,038
[45] Date of Patent: Jul. 1, 1997

[54] QUINONE DIAZO COMPOUND CONTAINING NON-METALLIC ATOM

[75] Inventors: Ari Aviram, Croton-on-Hudson; William Ross Brunsvold, Poughkeepsie, both of N.Y.; Daniel Bucca, Alexandria, Va.; Willard Earl Conley, Jr., Cornwall; David Earle Seeger, Congers, both of N.Y.

[73] Assignee: International Business Machines Corporation, Armonk, N.Y.

[21] Appl. No.: 616,599

[22] Filed: Mar. 15, 1996

Related U.S. Application Data

[62] Division of Ser. No. 314,975, Sep. 29, 1994, Pat. No. 5,552,256.

[51] Int. Cl.$^6$ ................................................. G03F 7/022
[52] U.S. Cl. ........................ 534/557; 534/556; 430/193
[58] Field of Search ................................. 534/557, 556; 430/191, 192, 193, 190, 169

[56] References Cited

U.S. PATENT DOCUMENTS

| | | | |
|---|---|---|---|
| 3,130,047 | 4/1964 | Uhlig et al. | 430/193 |
| 4,465,768 | 8/1984 | Ueno et al. | 430/296 |
| 4,588,671 | 5/1986 | Molodnyakov et al. | 430/191 |
| 4,661,434 | 4/1987 | Iwasaki et al. | 430/281 |
| 4,701,399 | 10/1987 | Nagano et al. | 430/179 |
| 4,883,739 | 11/1989 | Sakaguichi et al. | 430/192 |
| 5,066,564 | 11/1991 | Zertani et al. | 430/284 |
| 5,128,231 | 7/1992 | Itoh et al. | 430/270 |
| 5,130,392 | 7/1992 | Shwaim et al. | 526/288 |
| 5,141,841 | 8/1992 | Wade | 430/281 |
| 5,147,758 | 9/1992 | Smothers et al. | 430/281 |
| 5,151,341 | 9/1992 | Kim | 430/270 |
| 5,169,740 | 12/1992 | Ushirogouchi et al. | 430/192 |
| 5,358,824 | 10/1994 | Tan et al. | 430/192 |

FOREIGN PATENT DOCUMENTS

0524634A1  1/1993  European Pat. Off. .

OTHER PUBLICATIONS

Kwong et al., Highly Sensitive Positive Resist Systems for Lithographic Applications, IBM Technical Disclosure Bulletin, vol. 24, No. 12 (1982), pp. 6408–6410.

Shingo, Positive Type Photoresist Composition, Patent Abstracts of Japan, vol. 12, No. 235 (1988), and JP-A-63 027835.

Kalibabchuk et al., Effect of Substituent Nature on the Thermolysis of 1,2–Naphthoquinone 2–Diazide 5–Sulfonic Acid Esters, Chemical Abstracts, vol. 90, No. 11 (1979), Abstract No. 86469.

Martynenko et al., Interaction of radiation with materials, IV. Effect of halide atoms on the light sensitivity of aromatic diazo ketones, Chem. Abstracts, vol. 81, No. 17, (1974), Abstract No. 104333, pp. 431–432.

Lakhonina et al., Composition of Light–Sensitive Components of Positive Photoresists, Chem. Abstracts, vol. 110, No. 24, (1989), Abstract No. 222431, pp. 658.

*Primary Examiner*—Christopher G. Young
*Attorney, Agent, or Firm*—Pollock, Vande Sande & Priddy

[57] ABSTRACT

Quinone diazo compounds having bonded to the diazo ring or directly bonded to a ring of the compound, certain non-metallic atoms that improve the photosensitivity thereof are provided. These quinone diazo compounds are useful as photoactive compounds in photoresist compositions, and particularly positive photoresist composition employed in x-ray or electron beam radiation. Also provided is a method for preparing compounds of the present invention.

11 Claims, 2 Drawing Sheets

QUINONE DIAZO COMPOUND CONTAINING NON-METALLIC ATOM

This application is a divisional of U.S. patent application Ser. No. 08/314,975, filed Sep. 29, 1994, U.S. Pat. No. 5,552,256.

DESCRIPTION

1. Technical Field

The present invention is concerned with quinone diazo photoactive compounds that exhibit enhanced sensitivity to actinic light, and particularly to x-ray and electron beam exposure. In addition, the present invention is concerned with positive photoresist compounds that contain a positive acting organic polymer, along with the quinone diazo compounds that exhibit enhanced sensitivity. The present invention is particularly concerned with positive photoresist composition for x-ray lithography and/or electron beam lithography. The present invention makes it possible to achieve a more efficient lithographic process.

2. Background Art

In the manufacture of patterned devices, such as semiconductor chips and chip carriers, the steps of patterning different layers that constitute the finished product are among the most critical and crucial steps involved. This is particularly so in view of the trend toward very high integration densities and smaller devices. With respect to the production of smaller devices below 0.25 µm definition for integrated circuits, it is desirable, if not essential, to employ resist materials that can be used with radiation sources exhibiting short wavelengths. These short radiation sources operate in the x-ray region and include synchrotron and point sources. Also, electron beam lithography is employed for these smaller devices.

However, many of the conventional resist materials that are currently employed commercially are not especially sensitive to x-ray radiation or electron beam radiation. The inherent insensitivity of such resist materials makes the photospeed thereof too slow for practical application employing x-ray or electron beam lithography. More particularly, various compositions based on diazo quinone photoactive compounds do not perform satisfactorily as x-ray resists in view of their poor absorption of x-ray radiation. On the other hand, these resist compositions are widely used for UV radiation lithography.

Attempts to provide x-ray sensitive resists have resulted in what is referred to as chemically amplified resists material. An example of such is a hydroxylated polystyrene backbone, having attached thereto tert.butyl carbonate. Although these materials are sensitive to x-ray lithography, such suffer from the disadvantage that they are extremely sensitive to contaminants, such as degradation by acid and airborne amines. In fact, these chemically amplified resists are prone to poisoning by even ppm levels of contaminants. Therefore, the use of such requires extremely careful control of processing conditions. Because of the complexity in processing, it seems to be desirable to substitute these resists with nonamplified compositions.

SUMMARY OF INVENTION

It is therefore an object of the present invention to provide photoactive compounds that are suitable in x-ray lithography or electron beam lithography. In addition, it is an object of the present invention to provide materials for such purposes, which do not suffer from the problems experienced with chemically amplified resist materials. Furthermore, it is desirable to provide resist compositions that make it possible to employ derivatives of diazo quinone type photoactive compounds.

It has been found, pursuant to the present invention, that the bonding of certain non-metallic atoms to a quinone diazo compound enhances the sensitivity to x-ray radiation or electron beam radiation. More particularly, the present invention is concerned with a quinone diazo compound that contains bonded to a quinone diazo ring, or directly bonded to a ring of the compound, a non-metallic atom. The non-metallic atom can be Ge, As, I and Sb.

Another aspect of the present invention is concerned with positive photoresist compositions that contain a positive acting organic polymer, and a quinone diazo photoactive compound of the type disclosed hereinabove.

A still further object of the present invention is concerned with a method for forming a pattern of a photoresist. The method comprises providing on a substrate a layer of the above disclosed positive photoresist composition and imagewise exposing the layer to x-ray or electron beam radiation in a pattern to thereby cause dissolution of the photoresist that is exposed. Next, the photoresist is developed, typically in base, to thereby form the desired pattern.

A still further object of the present invention is directed to a process for producing a diazo quinone sulfonyl halide that contains an iodine atom bonded to a quinone diazo ring. The process comprises reacting an iododiazo quinone having an iodine atom bonded to a quinone diazo ring with sulfuric acid to thereby sulfonate the iododiazo quinone. The sulfonate is then converted to the desired sulfonyl halide.

BEST AND VARIOUS MODES FOR CARRYING OUT INVENTION

Figure 1:
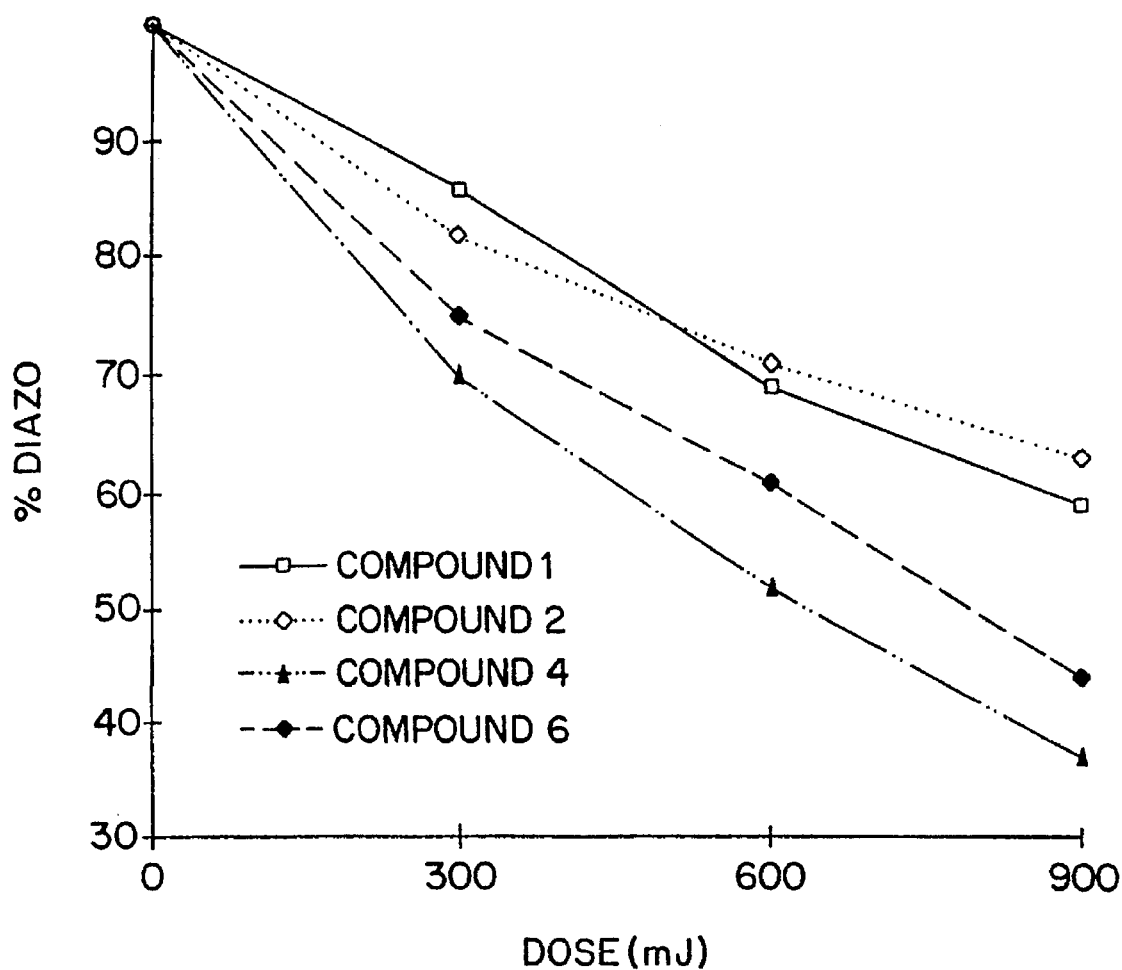
FIG. 1 illustrates the percent of photoactive compound versus radiation dose as determined by FTIR analysis.

It has been found, pursuant to the present invention, that the sensitivity of resist materials to x-ray radiation or electron beam radiation can be significantly improved by incorporating certain x-ray absorbing or electron beam absorbing atoms on diazo quinone photoactive compounds. The atoms employed are non-metallic atoms, selected from the group consisting of germanium, arsenic, iodine and antimony, and preferably iodine. These atoms are preferably bonded directly to a ring of the quinone diazo compound, or to a quinone diazo ring of the compound, and preferably, directly bonded on a quinone diazo ring of the compound. In addition, it is most preferred that these atoms be located at or near the photoactive component of the quinone diazo compound to thereby assure localization of the absorbed energy at the photoactive component of the compound. This in turn provides for the necessary energy for structural change of the compound, and for a most efficient lithographic process. Preferably, the non-metallic atom disclosed above should be located on a quinone diazo ring or as a linkage between rings that contain quinone diazo groups.

When the non-metallic atom, such as iodine, is bonded to a bridge that binds the quinone diazo groups, it is preferred that at least two such non-metallic atoms be employed.

The quinone diazo compounds employed in the present invention can be referred to as quinone diazide derivatives.

Usually, the quinone diazide employed are the ortho diazo naphthols, which are often referred to as the quinone-(1,2) diazides.

Examples of some quinone diazides include derivatives of 1,4-benzoquinone diazide; 1,2-benzoquinone diazide; 1,4-napthoquinone diazide; 1,2-naphthoquinone diazide; 2,1-naphthoquinone diazide; 1,8-naphthoquinone diazide; 1,7-naphthoquinone diazide; 1,6-naphthoquinone diazide; and 2,6-naphthoquinone diazide. In addition to the above described atoms that enhance the sensitivity of the compound, such derivatives also preferably include a sulfonyl moiety, such as sulfonyl chloride, sulfonyl bromide and sulfonyl iodine, or an acid group, such as sulfonic acid.

Examples of some quinone diazide structures that form the foundation of the derivatives employed pursuant to the present invention are as follows:

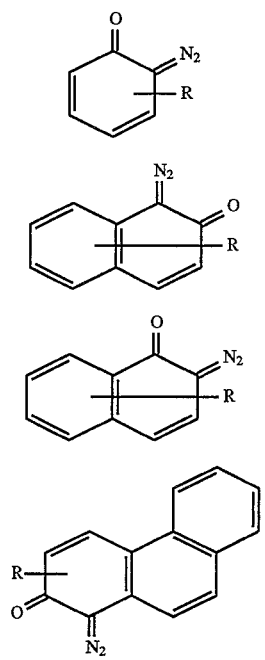

wherein R is $SO_2X$ and X is a halogen or other grouping, such as a ring configuration. In addition, one or more of the above rings can be a heterocyclic ring containing a member selected from the group of O, N, S or Se in the ring.

Examples of some preferred compounds employed pursuant to the present invention are represented by the following formulae:

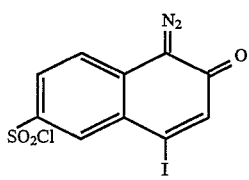 A

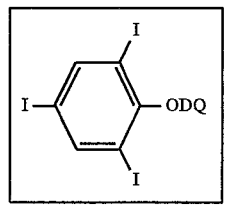 B

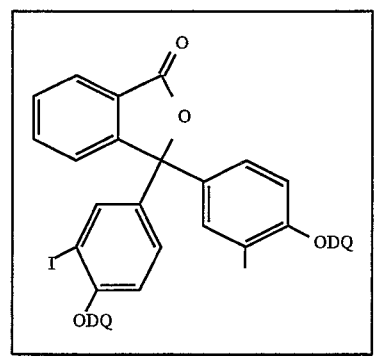 C

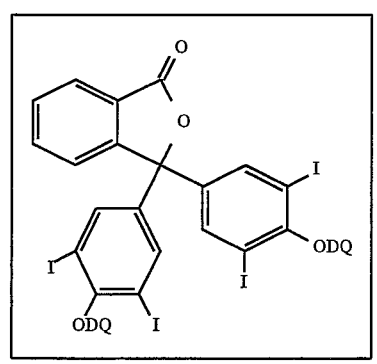 D

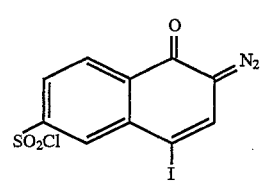 E

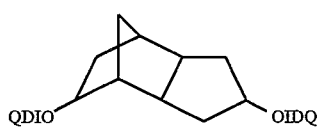 F wherein IDQ is an iodinated diazo quinone ring such as

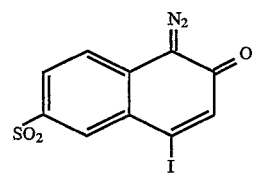

or any of the other iodinated diazo quinone rings.

The preferred compounds of the present invention are 4 iodonaphthalene-1,2-diazo-oxide-6-sulfonyl chloride and 4 iodonaphthalene-1,2-diazo-oxide-6-acyl chloride. In addition, the iodo group can be at the 5, 6, 7 or 8 position of the naphthalene ring.

Compounds employed pursuant to the present invention can be prepared by condensing hydroxide compounds, such as iodine containing hydroxy compounds, with quinone diazides containing a reactive group, such as sulfonyl halide group, such as sulfonyl chloride, or an acyl halide, such as acyl chloride. Examples of some suitable hydroxy compounds include phenols, naphthols and alcohols. Examples of some suitable quinone diazides are described hereinabove. A particular quinone employed is 2,1-diazo naphthoquinone sulfonyl chloride. Typically, stoichiometric amounts at normal room temperature are used.

The sulfonyl chloride, acyl chloride or similar compound is used for attaching the diazo quinone group to a bridge as shown in formulae B, C, D and F above. This provides the bridge

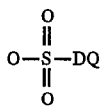

By way of example, the diazo quinone resists can employ a bridge, such as

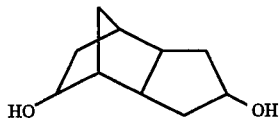

which is converted to the photoactive compound

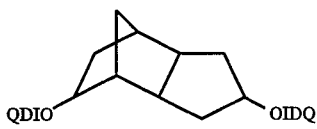

wherein IDQ can be

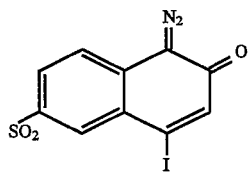

The photoactive compound can be obtained by reacting

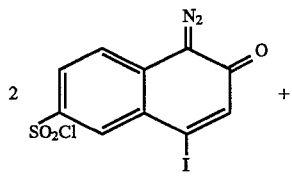

(OH)$_2$ bridge with a base such as Et$_3$N. The photoactive compound is then mixed with a polymer, such as a novolak to form the resist composition.

The most preferred compounds of the present invention, the diazo quinone sulfonyl halides, containing an iodine atom bonded to a quinone diazo ring, are prepared by reacting an iododiazo quinone having an iodine atom bonded to a quinone diazo ring, with a sulfuric acid, such as oleum, to thereby sulfonate the iododiazo quinone. The sulfonate is then converted to sulfonyl halide.

The positive photoresist compositions of the present invention also contain an organic polymer. Any of the known positive acting organic polymers employed can be used. Of particular importance are the phenolic formaldehyde novolaks and related derivatives, for example, meta-cresol is often employed as the phenolic component of the novolak. Poly(t-butyl oxycarbonyl oxystyrene) is another example of a suitable compound.

In the photoresist compositions, the quinone diazo photoactive compound is present in amounts sufficient to sensitize the polymer to the desired radiation. Typically, the amount of such is from about 5 to about 25, preferably from about 8 to about 10.

The solvent employed typically is propylene glycol monoether acetate (PGMEA).

When used as a lithographic composition, the compositions of the present invention are applied to a desired substrate to provide films generally about 1500 angstroms to 10 mils or more in thickness, such as by spraying, spinning, dipping, or any other known means of application of coating. Some suitable substrates include those used in the fabrication of semi-conductor devices, or integrated circuits, which include wafers or chips, overcoated with oxides and nitrides (silicon oxide and/or silicon nitride for diffusion masks and passivation) and/or metals normally employed in the metallization steps for forming contacts and conductor patterns on the semiconductor chip.

In addition, the compositions of the present invention can be used in conjunction with those substrates employable as chip carriers, and including ceramic substrates. Also included are dielectric substrates which can be thermoplastic and/or thermosetting polymers.

The compositions of the present invention after being coated to the desired thickness upon a substrate are exposed to the imaging radiation, such as the x-ray or electron beam radiation. After the imagewise exposure, the photoresist is developed, such as by contacting the exposed wafer with an aqueous alkaline solution, such as potassium hydroxide or tetramethylammonium hydroxide.

The following non-limiting examples are presented to illustrate the present invention:

EXAMPLE 1

Preparation of 4-iodonaphthalene-1,2-diazo-oxide-6-sulfonyl chloride

About 10 grams of 2-nitro-1-naphthylamine are dissolved in about 150 ml of acetic acid and heated to boiling. To this composition is added about 17.5 grams of a boiling aqueous solution of mercuric acetate, whereupon a precipitate forms. The precipitate is cooled, and 2-nitro-1 naphthylamine-4-merecuriacetate is obtained.

About 25 grams of this product are added to a 10% aqueous boiling solution of potassium iodide. Next, about 14 grams of iodine are added, and the mixture is boiled for about 5 minutes. Excess iodine is removed by adding sodium thiosulfate. A precipitate is formed and is filtered while hot, and then washed in hot water. It is recrystallized from methanol by soxhlet extraction to provide 4 iodo-2-nitro-1-naphthylamine.

About 6.3 grams of the 4-iodo-2-nitro-1-naphthylamine is dispersed in about 40 ml of glacial acetic acid. About 1.6 grams of sodium nitrite are added and the solution is stirred for about 30 minutes at about 30° C. The solution is then heated up to about 45° C. at 10° C./minute increments at which time, 0.2 grams of sodium nitrite are added. The solution is filtered and ice and water are added to the residue to cause precipitation of the product. The product, 4-iodonaphthalene-1,2-diazo-oxide, is recrystallized from methanol.

About 2.5 grams of 4-iodonaphthalene-1,2-diazo-oxide are added to a frozen mass of about 5 ml of sulfuric acid. The mixture is rotated as it is thermalized to room temperature, and is then refrozen. To this mixture is added about 10 ml of 20% oleum, and the mixture is rotated to cause stirring while it is thermalized. The mixture is then maintained at about room temperature for about 20 hours. The mixture is again refrozen and ice is added. The product, 4-iodonaphthalene-1,2-diazo oxide-6-sulfonic acid precipitates out. Additional water is added and the product is filtered, then washed with acetone, filtered again and then dried. About 0.37 grams of the 4-iodonaphthalene-1,2-diazo-oxide-6-sulfonic acid are dissolved in about 0.8 grams of chlorosulfonic acid. The solution is then heated to about 90° C. for about 10 minutes, then cooled and poured onto ice. The mixture is then extracted as fast as possible with ethyl acetate and dried over sodium sulfate. After removal of the solvent, the product is crystallized from ethyl acetate. The NMR spectrum run on the sample identifies it as 4-iodonaphthalene-1,2-diazo-oxide-6-sulfonyl chloride.

The photoactive compound (PAC) is compounded with a novolak resin to provide a composition containing 20% PAC and 80% novolak.

EXAMPLE 2

Photoactive compounds shown in Table 1 hereinbelow are prepared by reacting the corresponding iodine containing hydroxy compound with 2,1-diazo naphthoquinone sulfonyl chloride. The reaction is carried out employing triethylamine in methylene chloride with stirring for 2 hours and washing with 5% HCl aqueous solution followed by 5% NaHCO$_3$ aqueous solution. The solvent is then evaporated. Compound 1 shown in Table 1 below is the currently employed photoactive compound, and is used herein as a basis for comparison.

Resist compositions containing about 80% by weight of novolak resin and about 20% by weight of the identified photoactive compound are prepared. As apparent from Table 1, as the number of iodine per diazo quinone increases, the calculated absorbance of the molecule also increases. The absorbance of the bulk resist, however, is not greatly affected, due to the relatively small amount of photoactive compound material, typically found in a resist formulation.

As apparent from FIG. 1, a substantial improvement in sensitivity is achieved when employing at least two iodine atoms per diazo quinone group. In particular, see compounds 4 and 6. FIG. 1 shows the percent of photoactive compound versus the radiation dose, as determined by FTIR analysis. A substantial improvement of at least twice as much in the rate of decomposition with the higher number of iodine atoms. Since the increase in bulk resist absorption is less than about 4% when incorporated for instance, about 3 iodine atoms (see Compound 4, Table 1), the dramatic improvement in photospeed is attributable to an increase in localized energy provided relatively close to the diazo group of the photoactive compound.

TABLE 1

Photoactive Compounds and their Calculated Absorption for Synchrotron Radiation

| Compound[a] | Absorption[b] PAC | Resist[c] |
|---|---|---|
| 1[d] | 10% | 9% |
| 2 | 10% | 9% |
| 3 | 18% | 10.5% |
| 4 | 25% | 12.25% |
| 5 | 17% | 10.25% |
| 6 | 21% | 11.25% |

TABLE 1-continued

Photoactive Compounds and their Calculated Absorption for Synchrotron Radiation

| Compound[a] | Absorption[b] | |
|---|---|---|
| | PAC | Resist[c] |

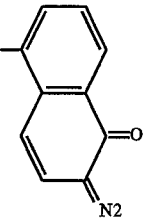

[a]Diazonaphthaquinone photoactive group DQ = —SO2—

[b]Calculated absorption assuming a one micron film and a density of one between the wavelengths 4.7–12 angstroms.
[c]Formulated resist consisting of 80% novolak and 20% PAC by weight. Note: the effect of iodine is diluted by novolak and consequently, the absorption of the resist is not greatly altered.
[d]PAC in current product.

EXAMPLE 3

Figure 2:
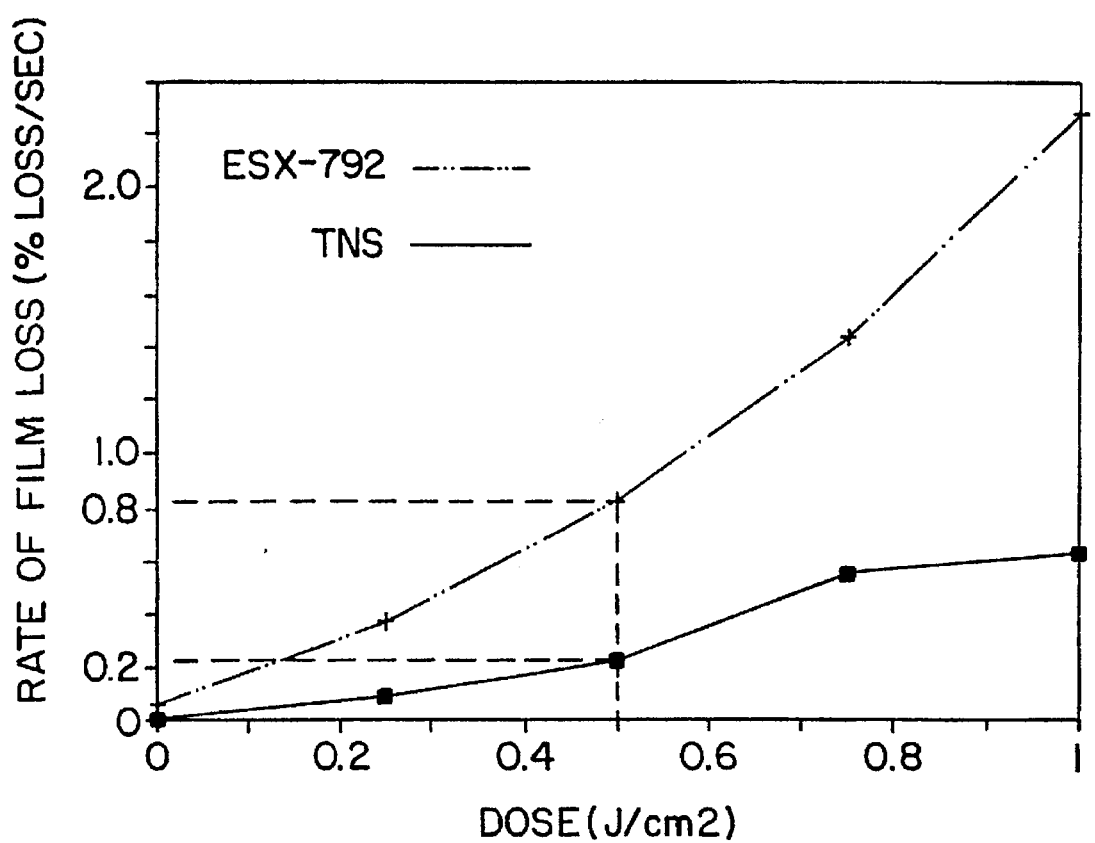
FIG. 2 is a plot of film loss versus dose for the photoresist.

A composition of about 80% by weight of novolak and about 20% by weight of the photoactive compound 4 shown in Table 1 is coated onto a silicon wafer and exposed to x-ray radiation, employing a synchrotron, and then developed in aqueous based developer. The thickness of the exposed regions (after post development) are measured and then converted to rate of film loss versus dosage. For a comparison purposes, commercially employed resist product TN5 is subjected to the same conditions. The results achieved are illustrated in FIG. 2. FIG. 2 is a plot of film loss versus dose for the photoresist. By comparison, it is clear that the present invention is considerably faster than the current standard employed.

What is claimed is:

1. A naphthoquinone diazo compound which contains directly bonded to the naphthalene of said compound at least one non-metallic atom selected from the group consisting of iodine, germanium, arsenic, antimony and mixtures thereof, wherein when iodine is said non-metallic atom it is bonded in at least the 4-position.

2. The compound of claim 1 which also includes a sulfonyl grouping.

3. The naphthoquinone diazo compound of claim 1 containing at least two non-metallic atoms.

4. The naphthoquinone diazo compound of claim 1 wherein said non-metallic atom is iodine.

5. A quinone-diazo compound selected from the group consisting of:

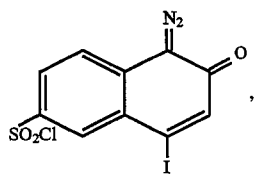

,

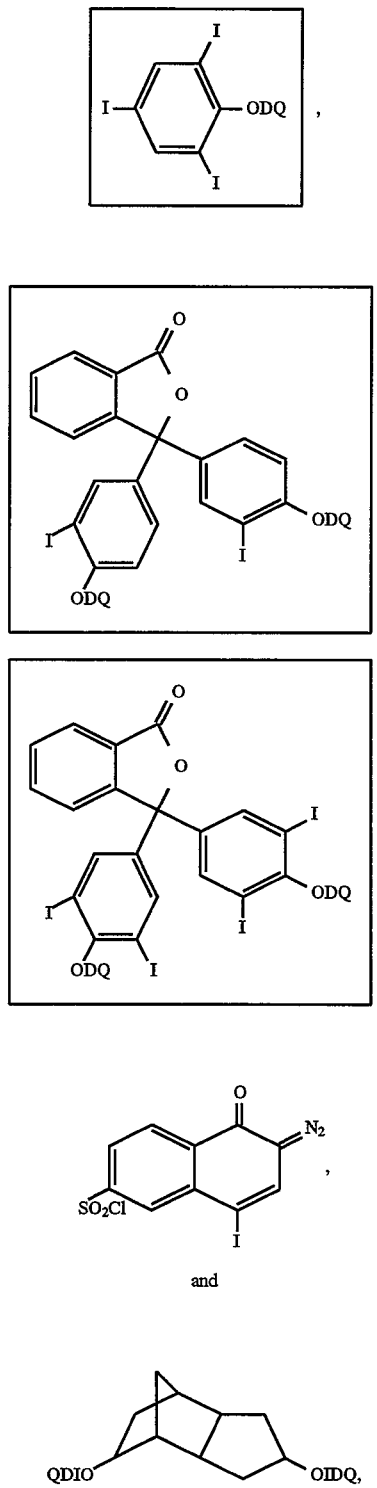

wherein DQ is a diazo quinone ring and wherein IDQ is an iodinated diazo quinone ring.

6. The quinone diazo compound of claim 5 being 4-iodonaphthalene-1,2-diazo-oxide-6-sulfonyl chloride.

7. The compound of claim 5 represented by the formula:
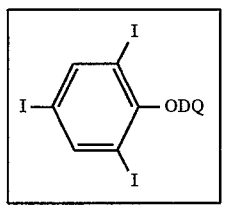 .
8. The compound of claim 5 represented by the formula:
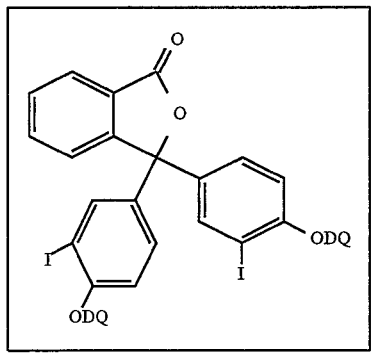 .
9. The compound of claim 5 represented by the formula:
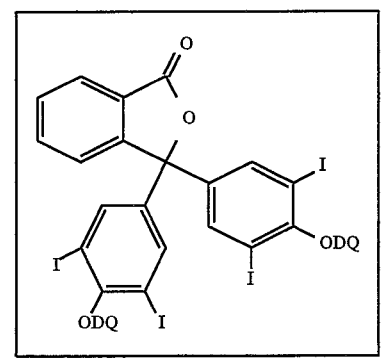 .
10. The compound of claim 5 represented by the formula:
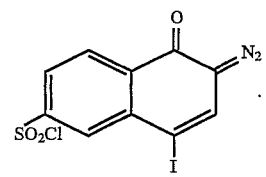 .
11. The compound of claim 5 represented by the formula:
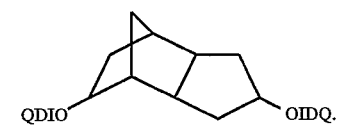 .
* * * * *